United States Patent
Cheung (10) Patent No.: US 12,380,967 B2
(45) Date of Patent: Aug. 5, 2025

(54) SYSTEM AND METHOD FOR AUTO-CONFIGURABLE DATA COMPRESSION FRAMEWORK

(71) Applicant: KONINKLIJKE PHILIPS N.V., Eindhoven (NL)

(72) Inventor: Yee Him Cheung, Boston, MA (US)

(73) Assignee: Koninklijke Philips N.V., Eindhoven (NL)

( * ) Notice: Subject to any disclaimer, the term of this patent is extended or adjusted under 35 U.S.C. 154(b) by 246 days.

(21) Appl. No.: 18/035,805

(22) PCT Filed: Nov. 11, 2021

(86) PCT No.: PCT/EP2021/081320
§ 371 (c)(1),
(2) Date: May 8, 2023

(87) PCT Pub. No.: WO2022/106289
PCT Pub. Date: May 27, 2022

(65) Prior Publication Data
US 2024/0013864 A1  Jan. 11, 2024

Related U.S. Application Data (60) Provisional application No. 63/226,791, filed on Jul. 29, 2021, provisional application No. 63/116,203, filed on Nov. 20, 2020.

(51) Int. Cl.
*G16B 50/50* (2019.01)
*G06F 16/174* (2019.01)
*H03M 7/30* (2006.01)

(52) U.S. Cl.
CPC ......... *G16B 50/50* (2019.02); *G06F 16/1744* (2019.01); *H03M 7/607* (2013.01); *H03M 7/6088* (2013.01)

(58) Field of Classification Search
CPC .... G16B 50/50; G06F 16/1744; H03M 7/607; H03M 7/6088
(Continued)

(56) References Cited

U.S. PATENT DOCUMENTS 6,624,761 B2 * 9/2003 Fallon ................. H03M 7/3059
341/51
10,727,864 B2 * 7/2020 Li ....................... H03M 7/3059

FOREIGN PATENT DOCUMENTS

| CN | 108306650 A | 7/2018 |
| EP | 2381579 A1 | 10/2011 |
| EP | 3229444 A1 | 10/2017 |

OTHER PUBLICATIONS

Anonymous "Data Compression" Wikipedia Nov. 19, 2020.
(Continued)

*Primary Examiner* — Khai M Nguyen (57) ABSTRACT

A method (100) for compressing and decompressing a data file, comprising: (i) receiving (120) a data file for compression comprising a plurality of different attributes; (ii) identifying (130) a first attribute of the plurality of different attributes; (iii) selecting (140) a plurality of compression types and/or configurations; (iv) compressing (150) at least some of the data from the received data file for the identified first attribute using each of the selected plurality of compression types and/or configurations; (v) determining (160) which one of the selected plurality of compression types and/or configurations is most suitable for compression; (vi) generating (170) a compression parameter data structure comprising an identification of the selected plurality of compression types and/or configurations; (vii) compressing (180) the data from the received data file for the first attribute to generate a compressed data file; and (viii) storing (190) the compression parameter data structure and the compressed data file.

14 Claims, 3 Drawing Sheets

(58) Field of Classification Search
USPC .............................................. 341/50–51, 87
See application file for complete search history.

(56) References Cited

OTHER PUBLICATIONS

Anonymous "Image Compression" Wikipedia Sep. 9, 2020.
International Search Report and Written Opinion from PCT/EP2021/081320 Mailed Feb. 24, 2022.
Shubham Chandak et al., "Proposal of a Unified File Format for the Coding of Genomic Annotations", 129. MPEG Meeting, Jun. 2020. https://www.philips.com/c-dam/corporate/en_AA/about/about-us/ip-s/standardization/documents/m54565-proposed-enhancements-to-working-draft-of-mpeg-g-part-6.pdf.

* cited by examiner

```
##fileformat=VCFv4.3
##fileDate=20090805
##source=myImputationProgramV3.1
##reference=file:///seq/references/1000GenomesPilot-NCBI36.fasta
##contig=<ID=20,length=62435964,assembly=B36,md5=f126cdf8a6e0c7f379d618ff66beb2da,species="Homo sapiens",taxonomy=x>
##phasing=partial
##INFO=<ID=NS,Number=1,Type=Integer,Description="Number of Samples With Data">
##INFO=<ID=DP,Number=1,Type=Integer,Description="Total Depth">
##INFO=<ID=AF,Number=A,Type=Float,Description="Allele Frequency">
##INFO=<ID=AA,Number=1,Type=String,Description="Ancestral Allele">
##INFO=<ID=DB,Number=0,Type=Flag,Description="dbSNP membership, build 129">
##INFO=<ID=H2,Number=0,Type=Flag,Description="HapMap2 membership">
##FILTER=<ID=q10,Description="Quality below 10">                                      310
##FILTER=<ID=s50,Description="Less than 50% of samples have data">
##FORMAT=<ID=GT,Number=1,Type=String,Description="Genotype">
##FORMAT=<ID=GQ,Number=1,Type=Integer,Description="Genotype Quality">
##FORMAT=<ID=DP,Number=1,Type=Integer,Description="Read Depth">
##FORMAT=<ID=HQ,Number=2,Type=Integer,Description="Haplotype Quality">
#CHROM POS     ID        REF  ALT   QUAL FILTER INFO                                FORMAT      NA00001          NA00002          NA00003
20     14370   rs6054257 G    A     29   PASS   NS=3;DP=14;AF=0.5;DB;H2             GT:GQ:DP:HQ 0|0:48:1:51,51   1|0:48:8:51,51   1/1:43:5:.,.
20     17330   .         T    A     3    q10    NS=3;DP=11;AF=0.017                 GT:GQ:DP:HQ 0|0:49:3:58,50   0|1:3:5:65,3     0/0:41:3
20     1110696 rs6040355 A    G,T   67   PASS   NS=2;DP=10;AF=0.333,0.667;AA=T;DB   GT:GQ:DP:HQ 1|2:21:6:23,27   2|1:2:0:18,2     2/2:35:4
20     1230237 .         T    .     47   PASS   NS=3;DP=13;AA=T                     GT:GQ:DP:HQ 0|0:54:7:56,60   0|0:48:4:51,51   0/0:61:2
20     1234567 microsat1 GTC  G,GTCT 50  PASS   NS=3;DP=9;AA=G                      GT:GQ:DP    0/1:35:4         0/2:17:2         1/1:40:3
```

FIG. 3

SYSTEM AND METHOD FOR AUTO-CONFIGURABLE DATA COMPRESSION FRAMEWORK

CROSS REFERENCE TO RELATED APPLICATIONS

This application is a U.S. national phase application of International Application No. PCT/EP2021/081320 filed on Nov. 11, 2021, which claims the benefit of U.S. Application Ser. No. 63/116,203 filed on Nov. 20, 2020 and U.S. Application Ser. No. 63/226,791 filed on Jul. 29, 2021 and are incorporated herein by reference.

FIELD OF THE DISCLOSURE

The present disclosure is directed generally to methods and systems for compressing a data file using a file compression/decompression system.

BACKGROUND

Given the ever-growing size of many data files, efficient file compression methods and systems are increasingly important. A single genomic data file, for example, can comprise sequencing results for millions or billions of locations across the genomes of numerous samples, with annotations and other data attributes. A Variant Call Format (VCF) file, for example, can comprise gene sequence variations with millions of rows and numerous columns comprising data attributes. These data files must be stored for a long time, and will be very large in size sometimes being 100s or 1000s of gigabytes.

Compression of a data file typically comprises one or more data compressors. While there are numerous generic compressors that can be applied directly to a data file, their compression performances are usually suboptimal since they do not fully exploit the similarity or predictability of the data of individual fields within the dataset for the effective removal of data redundancy. One approach for improving compression ratio is therefore first dividing a dataset into fields with distinct characteristics, and then compressing each of the fields individually with a compressor that can take the most advantage of the specific data model of the field. However, this generally requires that the data fields and their associated compressors be pre-determined for each and every file type, and the encoding and decoding processes to be hardcoded accordingly in the software used for compression and decompression. The rigidity of such an approach makes it difficult to accommodate emerging data types or adopt new algorithms.

SUMMARY OF THE DISCLOSURE

There is a continued need for methods and systems for efficient and adaptable compression and decompression of data files. The present disclosure is directed to inventive methods and systems for compressing a data file using automated identification and/or configuration of data compressors based on compression performance. A file compression/decompression system receives a data file for compression comprising a plurality of different attributes for each of a plurality of different samples. The system identifies a first attribute of the plurality of different attributes, and selects a plurality of different compression types and/or compression configurations from a predetermined plurality of compression types and configurations based on the first attribute. The system compresses data from the received genomic data file for the identified first attribute using each of the selected plurality of compression types and/or compression configurations, individually, and determines which one of the selected plurality of compression types and/or compression configurations is most suitable for compression. Then the system generates a compression parameter data structure comprising an identification of the one of the selected plurality of compression types and/or compression configurations most suitable for compression of the identified first attribute, and compresses the data from the received genomic data file for the first attribute to generate a compressed genomic data file using the identified compression type and/or compression configuration. The compression parameter data structure and the compressed genomic data file are then stored and can be used for decompression.

Generally, in one aspect, a method for compressing/decompressing a genomic data file using a file compression/decompression system is provided. The method includes: (i) receiving a data file for compression, the data file comprising a plurality of different attributes; (ii) identifying a first attribute of the plurality of different attributes, and storing a specification of the identified first attribute in an attribute parameter data structure; (iii) selecting, based on the identified first attribute, a plurality of compression types and/or compression configurations from a predetermined plurality of compression types and/or compression configurations; (iv) compressing at least some of the data from the received data file for the identified first attribute using each of the selected plurality of compression types and/or compression configurations, individually, wherein one or more metrics are measured for each individual compression; (v) determining, based on the one or more metrics of each of the individual compressions, which one of the selected plurality of compression types and/or compression configurations is most suitable for compression; (vi) generating a compression parameter data structure comprising an identification of the one of the selected plurality of compression types and/or compression configurations most suitable for compression of the identified first attribute; (vii) compressing, using the identified compression type, the data from the received data file for the first attribute to generate a compressed data file; and (viii) storing the attribute parameter data structure, the compression parameter data structure and the compressed data file, wherein the stored compression parameter data structure is configured to be retrieved and used for decompression of the compressed data file.

According to an embodiment, the method further includes repeating the identifying, selecting, compression, and determining steps for at least a second attribute of the plurality of different attributes, wherein the compression parameter data structure comprises a specification of a one of the selected plurality of compression types and/or compression configurations most suitable for compression of the identified second attribute.

According to an embodiment, the method further includes decompressing the stored compressed data file, wherein decompression comprises consulting the compression parameter data structure to identify a decompression type for the first attribute.

According to an embodiment, each of the selected plurality of compression types and/or compression configurations is selected because it is capable of compressing the data from the received data file for the identified first attribute.

According to an embodiment, the data file is a genomic data file.

According to an embodiment, the one or more metrics comprises one or more of compression ratio and processing time for said compression.

According to an embodiment, a compression type is most suitable when the corresponding compression comprises a higher compression ratio and/or a faster processing time relative to the other of the plurality of selected compression types and/or compression configurations.

According to an embodiment, the method further includes providing, via a user interface, information about the generated compression parameter data structure and/or the compressed data file.

According to an embodiment, the method further includes providing to a user, via a user interface, information about one or more of the identified compression types and/or compression configurations such that the user can select a compressor type and/or configuration to be applied to compress an attribute.

According to a second aspect is a system for compressing/decompression a data file. The system includes: a data file for compression, the data file comprising a plurality of different attributes; and a processor configured to: (i) identify a first attribute of the plurality of different attributes and store a specification of the identified first attribute in an attribute parameter data structure; (ii) select, based on the identified first attribute, a plurality of compression types and/or compression configurations from a predetermined plurality of compression types and/or compression configurations; (iii) compress at least some of the data from the received data file for the identified first attribute using each of the selected plurality of compression types and/or compression configurations, individually, wherein one or more metrics are measured for each individual compression; (iv) determine, based on the one or more metrics of each of the individual compressions, which one of the selected plurality of compression types and/or compression configurations is most suitable for compression; (v) generate a compression parameter data structure comprising an identification of the one of the selected plurality of compression types and/or compression configurations most suitable for compression of the identified first attribute; (vi) compress, using the identified compression type, the data from the received data file for the first attribute to generate a compressed data file; and (vii) store the attribute parameter data structure, the compression parameter data structure and the compressed data file, wherein the stored compression parameter data structure is configured to be retrieved and used for decompression of the compressed data file.

According to an embodiment, the system comprises a user interface configured to provide information about the generated compression parameter data structure and/or the compressed data file.

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects as discussed herein. The terms "program" or "computer program" are used herein in a generic sense to refer to any type of computer code (e.g., software or microcode) that can be employed to program one or more processors or controllers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

FIG. 3 is a schematic representation of a data file, in accordance with an embodiment.

DETAILED DESCRIPTION OF EMBODIMENTS

The present disclosure describes various embodiments of a system and method for efficient and adaptable compression of data files. Applicant has recognized and appreciated that it would be beneficial to provide a data file compression method and system that employs automated identification and/or configuration of data compressors based on compression performance. A data file compression/decompression system receives a genomic data file for compression, the genomic data file comprising a plurality of different attributes (or data fields) for each of a plurality of different genomic samples. The system identifies a first attribute of the plurality of different attributes and selects, based on that attribute, a plurality of compression types and/or compression configurations from a predetermined plurality of compression types and compression configurations, wherein each of the selected plurality of compression types and/or compression configurations is capable of compressing the data from the received genomic data file for the identified first attribute. The data file compression system compresses at least some of the data from the received genomic data file for the identified first attribute using each of the selected plurality of compression types and/or compression configurations, individually, wherein one or more metrics are measured for each individual compression, the one or more metrics comprising one or more of compression ratio and processing time for said compression. Based on the one or more metrics of each of the individual compressions, the system determines which one of the selected plurality of compression types and/or compression configurations is most suitable for compression. According to an embodiment, a compression type is most suitable when the corresponding compression comprises a higher compression ratio and/or a faster processing time relative to the other of the plurality of selected compression types and/or compression configurations. The system then generates a compression parameter data structure comprising an identification of and/or the processing instructions for the one of the selected plurality of compression types and/or compression configurations most suitable for compression of the identified first attribute, and compresses the from the received genomic data file for the first attribute to generate a compressed genomic data file. The compression parameter data structure and the compressed genomic data file are stored, where the stored compression parameter data structure is configured to be retrieved and used for decompression of the compressed genomic data file.

According to an embodiment, the novel methods and systems described or otherwise envisioned herein provide a framework for the automatic configuration of compressors for data fields based on their performances, and enable compressors to be specified explicitly and stored along with compressed data. To access attribute data, a decoder can execute decompression and inverse transform algorithms based on the processing steps and parameters specified in the compressor configuration associated with the attribute. The novel methods and systems described or otherwise envisioned herein provide numerous advantages. For example, the methods and systems provide flexibility for customizing compressor configurations for a file, and ease the adoption of new transform and compression algorithms. Second, the methods and systems accommodate any new file types by identifying and providing compressor configurations. Since processing instructions are contained in the compressor configurations and not hardcoded in the software, a decoder can readily process a file without the need for modifications of codes. Third, auto-configuration of compressor settings helps to improve compression performance without requiring user knowledge or experience. The methods and systems provide many other advantages as well.

According to an embodiment, the compressor configuration framework system comprises one or more of the following components: (i) a uniform data interface for specifying a compressor, such as a compression process that consists of a sequence of data transform and compression steps and their default parameters; (ii) a uniform data interface for specifying a data attribute and associating it to a compressor with customized parameters; (iii) an algorithm for encoding attribute data based on the processing steps specified in the associated compressor configuration; (iv) an algorithm for decoding attribute data based on the processing steps specified in the associated compressor configuration; and (v) a mechanism for the automatic determination of compressor configurations based on performance.

Figure 1:
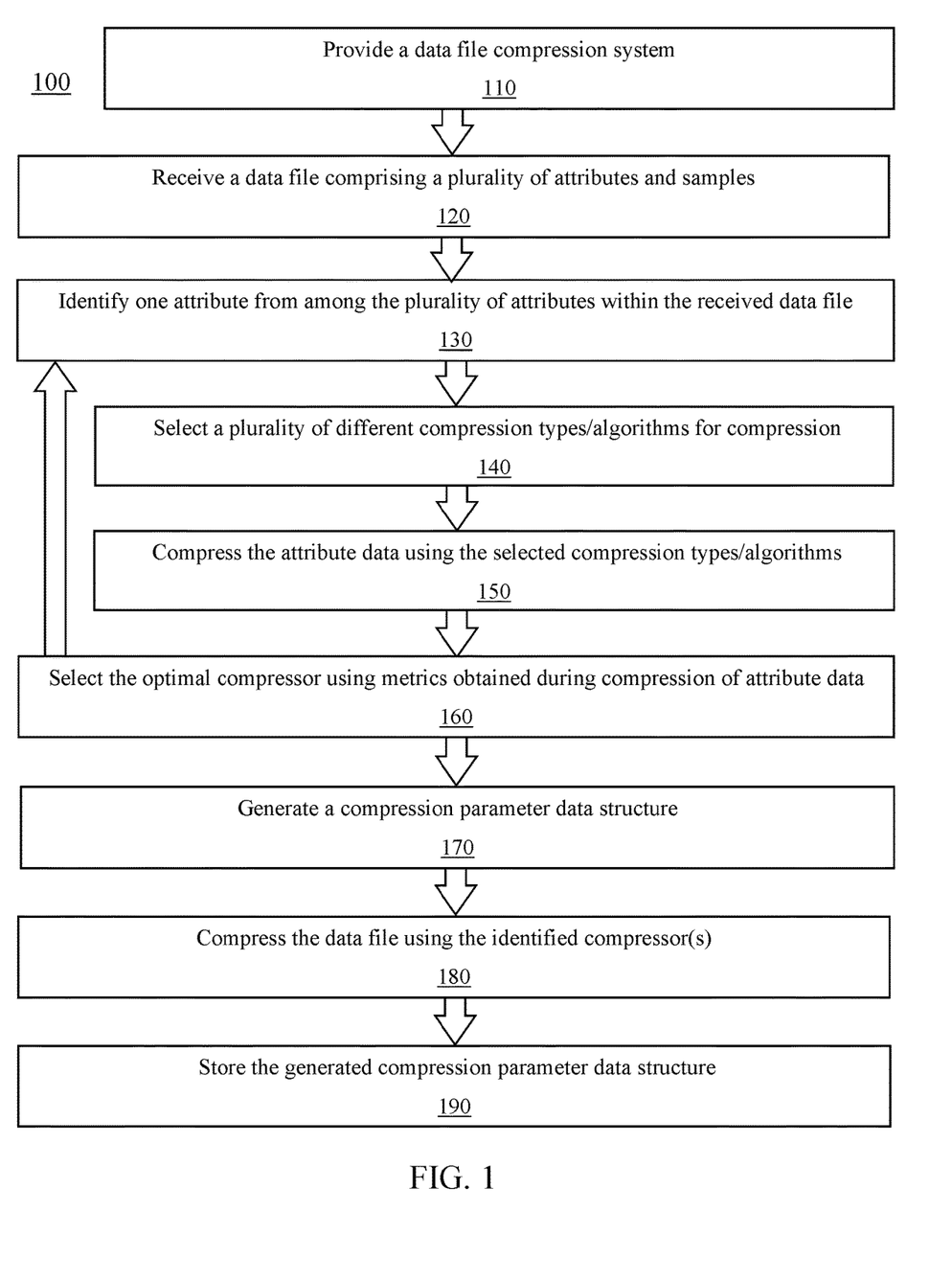
FIG. 1 is a flowchart of a method for compressing a genomic data file using a file compression/decompression system, in accordance with an embodiment.

Referring to FIG. 1, in one embodiment, is a flowchart of a method 100 for compressing a genomic data file using a file compression/decompression system. The methods described in connection with the figures are provided as examples only, and shall be understood not to limit the scope of the disclosure. The file compression/decompression system can be any of the systems described or otherwise envisioned herein. The file compression/decompression system can be a single system or multiple different systems.

Figure 2:
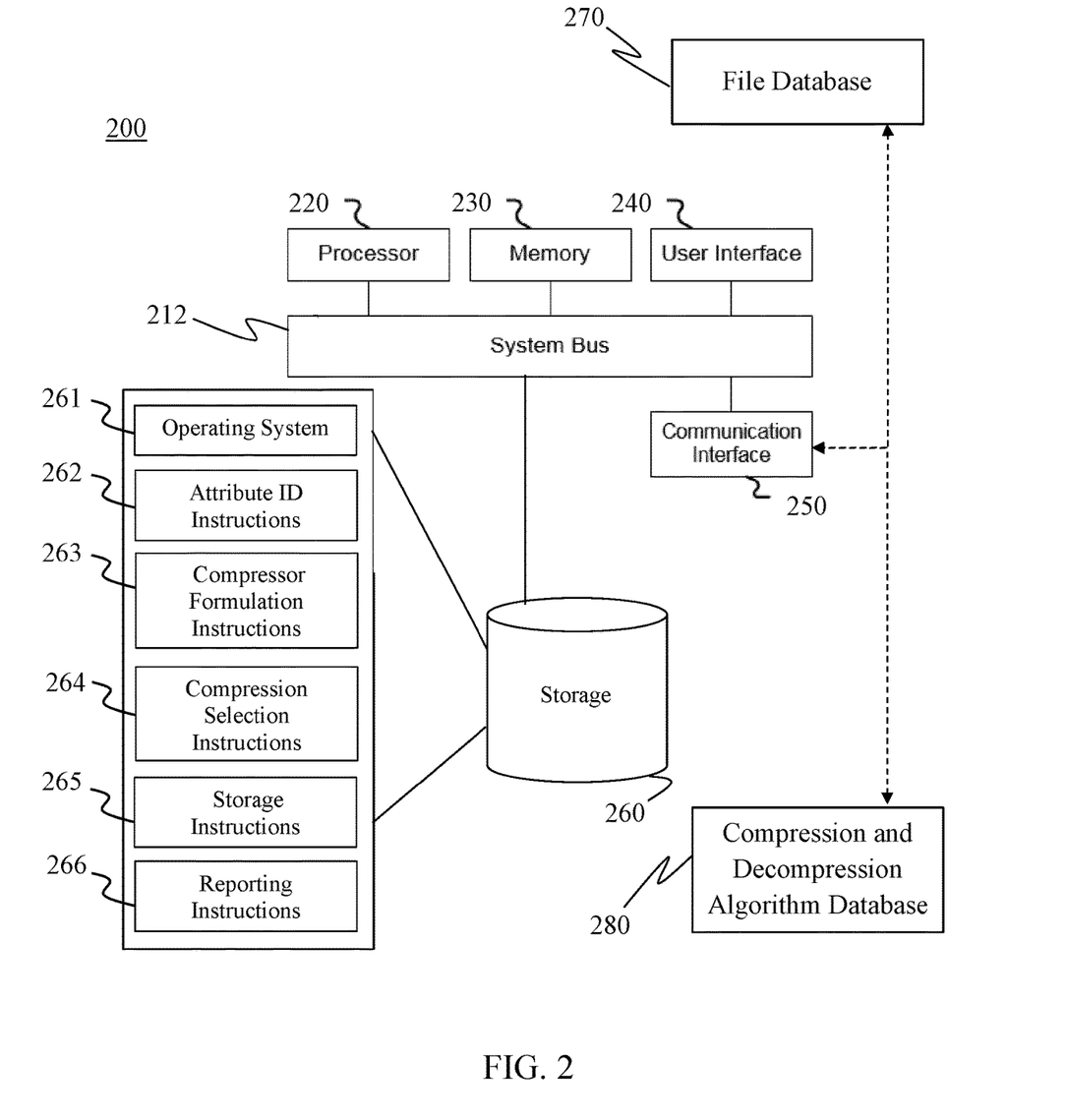
FIG. 2 is a schematic representation of a file compression/decompression system, in accordance with an embodiment.

At step 110 of the method, a file compression/decompression system 200 is provided. Referring to an embodiment of a file compression/decompression system 200 as depicted in FIG. 2, for example, the system comprises one or more of a processor 220, memory 230, user interface 240, communications interface 250, and storage 260, interconnected via one or more system buses 212. It will be understood that FIG. 2 constitutes, in some respects, an abstraction and that the actual organization of the components of the system 200 may be different and more complex than illustrated. Additionally, file compression/decompression system 200 can be any of the systems described or otherwise envisioned herein. Other elements and components of the file compression/decompression system 200 are disclosed and/or envisioned elsewhere herein.

According to an embodiment, file compression/decompression system 200 comprises or is in direct or indirect communication with a file database 270. The file database comprises, among other possible data, one or more files that can be compressed, or have been compressed, using the file compression/decompression system 200. According to one embodiment, the one or more files comprise genomic files, with a genomic file comprising gene sequence variations with millions of rows and numerous columns comprising data attributes, potentially for many different genomic samples. The file database can be any such database, including but not limited to the databases and systems described or otherwise envisioned herein.

According to an embodiment, file compression/decompression system 200 comprises or is in direct or indirect communication with a compression and decompression algorithm database 280. The compression and decompression algorithm database comprises a library of different compression algorithms and decompression algorithms. These compression and decompression algorithms can be utilized to compress and decompress the data files by the data file system. New compression algorithms and decompression algorithms can be added to the database at any time. The compression and decompression algorithm database can be any such database, including but not limited to the databases and systems described or otherwise envisioned herein.

At step 120 of the method, the file compression/decompression system receives an uncompressed data file for compression, the data file comprising a plurality of different attributes for each of a plurality of different samples. For genomic data files, as an example, the genomic data file comprises a plurality of different attributes for each of a plurality of different genomic samples. The data file can be received locally or remotely from any source, including but not limited to the file database 270, which itself can be a local or remote database.

At step 130 of the method, the file data system identifies a first attribute among the plurality of different attributes in the data file. An attribute can be any information from the data file. Referring to FIG. 3, in one non-limiting example of a data file, is a portion 300 of a genomic data file comprising a plurality of columns 310 where each column is an attribute. The file data system can be configured to recognize known attributes within a data file, or can be configured to predict or estimate or otherwise determine new or unrecognized attributes within a data file. Accordingly, the file data system can be configured to identify a first attribute among a plurality of different attributes in a data file using a wide variety of different methods. According to an embodiment, after identifying an attribute, the system specifies the attribute in an attribute parameter data structure (such as Attribute Parameter Set described herein).

At step 140, the data file compression/decompression system selects a plurality of compression types or algorithms (a "compressor") and/or compression configurations from a predetermined plurality of compression types, algorithms, and configurations. A compressor or compression configuration can comprise, for example, a sequence of compression algorithms and the parameter(s) associated with the compression algorithms. The compression types, algorithms, and compression configurations can be selected locally or remotely from any source, including but not limited to the compression and decompression algorithm database 280, which itself can be a local or remote database. According to an embodiment, one or more of the plurality of compression types, algorithms, and compression configurations is selected from the predetermined plurality of compression types, algorithms, and compression configurations based at least in part on the identified attribute. For example, a compressor or configuration may be selected based on the ability of the compressor to compress the data from the received data file for the identified first attribute. Thus, the system may preferentially identify compressors or configurations capable of compressing the first attribute data, and/or may preferentially exclude compressors incapable of compressing the first attribute data.

At step 150, the file data system compresses data using the identified compressors. According to an embodiment, the file compression/decompression system individually compresses the first attribute data. This individual compression by the plurality of compressors can be performed sequentially or simultaneously. According to an embodiment, each compressor compresses only a subset of the first attribute data, where the subset is an identical subset for each compressor in order to allow for more objective comparison of compression metrics among the plurality of compressors. According to another embodiment, each compressor compresses all of the first attribute data.

According to embodiment, the file compression/decompression system measures or otherwise obtains or identifies one or more compression metrics for each individual compression by each compressor. This enables objective comparison of compression performance among the plurality of compressors, and the selection of a preferred compressor for the first attribute data. According to an embodiment, compression metrics can be compression ratio, processing time, compression accuracy, and/or any other compression metric.

At step 160 of the method, the file compression/decompression system determines which of the selected plurality of compression types, algorithms, or compression configurations is most suitable for compression, using the measured or obtained metrics. Accordingly, the file compression/decompression system compares, ranks, or otherwise utilizes the metrics corresponding to each individual compressor and selects a preferred compressor. For example, a compressor or configuration may be most suitable or preferred for compression when the compression or configuration comprises a higher or best compression ratio and/or a faster processing time relative to the other of the plurality of selected compression types or configurations. According to a first embodiment, the file compression/decompression system is configured to select the compressor with the best compression ratio. According to a second embodiment, the file compression/decompression system is configured to select the compressor with the fastest compression or processing time. According to a third embodiment, the file compression/decompression system is configured to select the compressor with the best combination of compression ratio and compression or processing time. These configurations can be preprogrammed, can be learned, or can be determined by a user of the system, among other options.

According to an embodiment, the file compression/decompression system repeats these identifying, selecting, compression, and determining steps for one or more additional attributes. For example, the system can be configured to identify a preferred compressor for some or all attributes found within the data file.

At step 170 of the method, the file compression/decompression system generates a compression parameter data structure, such as a compression parameter data file. According to an embodiment, the generated compression parameter data structure comprises an identification of and/or specification(s) for the selected compressor and/or compression configurations for at least the first identified attribute, and optionally an identification of the compressor(s) and/or compression configuration(s) selected for a plurality of attributes in the data file (for example, specifying the use of a compressor for multiple attributes). The compression parameter data file can comprise any information necessary to utilize a compressor, including compressor settings and other information.

At step 180 of the method, the file compression/decompression system compresses the data from the received data file to generate a compressed data file, using the identified compressor(s) and/or compression configuration(s). Accordingly, this can comprise the compression of first attribute data, data for multiple attributes, or data for all attributes in the file. Once the system generates a compressed data file, the file can be utilized immediately, such as sending or otherwise transmitting or using the compressed file, or the compressed file can be stored in local or remote storage for use in further steps of the method. Many other options are possible.

At step 190 of the method, the generated compression parameter data structure is stored such that the stored file can be retrieved and used for decompression of the compressed data file. The compression parameter data structure can be stored in a remote or local database which can be a component of or otherwise in communication with file compression/decompression system 200. For example, the compression parameter data structure can be stored together with the compressed data file, or stored with a reference to or from the compressed data file.

Referring to FIG. 2, in one embodiment, is a schematic representation of a file compression/decompression system 200. System 200 may be any of the systems described or otherwise envisioned herein, and may comprise any of the components described or otherwise envisioned herein. It will be understood that FIG. 2 constitutes, in some respects, an abstraction and that the actual organization of the components of the system 200 may be different and more complex than illustrated.

According to an embodiment, system 200 comprises a processor 220 capable of executing instructions stored in memory 230 or storage 260 or otherwise processing data to, for example, perform one or more steps of the method. Processor 220 may be formed of one or multiple modules. Processor 220 may take any suitable form, including but not limited to a microprocessor, microcontroller, multiple microcontrollers, circuitry, field programmable gate array (FPGA), application-specific integrated circuit (ASIC), a single processor, or plural processors.

Memory 230 can take any suitable form, including a non-volatile memory and/or RAM. The memory 230 may include various memories such as, for example L1, L2, or L3 cache or system memory. As such, the memory 230 may include static random access memory (SRAM), dynamic RAM (DRAM), flash memory, read only memory (ROM), or other similar memory devices. The memory can store, among other things, an operating system. The RANI is used by the processor for the temporary storage of data. According to an embodiment, an operating system may contain code which, when executed by the processor, controls operation of one or more components of system 200. It will be apparent that, in embodiments where the processor implements one or more of the functions described herein in hardware, the software described as corresponding to such functionality in other embodiments may be omitted.

User interface 240 may include one or more devices for enabling communication with a user. The user interface can be any device or system that allows information to be conveyed and/or received, and may include a display, a mouse, and/or a keyboard for receiving user commands. In some embodiments, user interface 240 may include a command line interface or graphical user interface that may be presented to a remote terminal via communication interface 250. The user interface may be located with one or more other components of the system, or may located remote from the system and in communication via a wired and/or wireless communications network.

Communication interface 250 may include one or more devices for enabling communication with other hardware devices. For example, communication interface 250 may include a network interface card (MC) configured to communicate according to the Ethernet protocol. Additionally, communication interface 250 may implement a TCP/IP stack for communication according to the TCP/IP protocols. Various alternative or additional hardware or configurations for communication interface 250 will be apparent.

Storage 260 may include one or more machine-readable storage media such as read-only memory (ROM), random-access memory (RANI), magnetic disk storage media, optical storage media, flash-memory devices, or similar storage media. In various embodiments, storage 260 may store instructions for execution by processor 220 or data upon which processor 220 may operate. For example, storage 260 may store an operating system 261 for controlling various operations of system 200.

It will be apparent that various information described as stored in storage 260 may be additionally or alternatively stored in memory 230. In this respect, memory 230 may also be considered to constitute a storage device and storage 260 may be considered a memory. Various other arrangements will be apparent. Further, memory 230 and storage 260 may both be considered to be non-transitory machine-readable media. As used herein, the term non-transitory will be understood to exclude transitory signals but to include all forms of storage, including both volatile and non-volatile memories.

While system 200 is shown as including one of each described component, the various components may be duplicated in various embodiments. For example, processor 220 may include multiple microprocessors that are configured to independently execute the methods described herein or are configured to perform steps or subroutines of the methods described herein such that the multiple processors cooperate to achieve the functionality described herein. Further, where one or more components of system 200 is implemented in a cloud computing system, the various hardware components may belong to separate physical systems. For example, processor 220 may include a first processor in a first server and a second processor in a second server. Many other variations and configurations are possible.

According to an embodiment, file compression/decompression system 200 comprises or is in direct or indirect communication with a file database 270. The file database comprises, among other possible data, one or more files that can be compressed, or have been compressed, using the file compression/decompression system 200. According to one embodiment, the one or more files comprise genomic files, with a genomic file comprising gene sequence variations with millions of rows and numerous columns comprising data attributes, potentially for many different genomic samples.

According to an embodiment, file compression/decompression system 200 comprises or is in direct or indirect communication with a compression and decompression algorithm database 280. The compression and decompression algorithm database comprises a library of different compression algorithms and decompression algorithms. These compression and decompression algorithms can be utilized to compress and decompress the data files by the data file system. New compression algorithms and decompression algorithms can be added to the database at any time.

According to an embodiment, storage 260 of system 200 may store one or more algorithms, modules, and/or instructions to carry out one or more functions or steps of the methods described or otherwise envisioned herein. For example, storage 260 may comprise, among other instructions or data, attribute identification instructions 262, compressor formulation instructions 263, compressor selection instructions 264, storage instructions 265, and/or reporting instructions 266.

According to an embodiment, attribute identification instructions 262 direct the system to identify an attribute among a plurality of different attributes in a data file received by the system. An attribute can be any information from the data file. The file data system can be configured to recognize known attributes within a data file or can be configured to predict or estimate or otherwise determine new or unrecognized attributes within a data file. Accordingly, the file data system can be configured to identify a first attribute among a plurality of different attributes in a data file using a wide variety of different methods.

According to an embodiment, compressor formulation instructions 263 direct the system to select a plurality of compressors from a predetermined plurality of compression types, algorithms, and/or compression configuration(s). The compression types, algorithms, and/or compression configuration(s) can be selected locally or remotely from any source, including but not limited to the compression and decompression algorithm database 280. The compressor formulation instructions 263 also direct the system to compress some or all of the attribute data using the identified compressors and/or compression configuration(s) individually. This individual compression by the plurality of compressors can be performed sequentially or simultaneously. According to an embodiment, each compressor compresses only a subset of the first attribute data, where the subset is an identical subset for each compressor in order to allow for more objective comparison of compression metrics among the plurality of compressors. According to another embodiment, each compressor compresses all of the first attribute data.

According to embodiment, compressor formulation instructions 263 also direct the system to measure or otherwise obtain or identify one or more compression metrics for each individual compression by each compressor. This enables objective comparison of compression performance among the plurality of compressors and/or compression configuration(s), and the selection of a preferred compressor and/or compression configuration for the first attribute data. According to an embodiment, compression metrics can be compression ratio, processing time, compression accuracy, and/or any other compression metric.

According to an embodiment, compressor selection instructions 264 direct the system to determine which of a selected plurality of compression types, algorithms, and/or compression configuration(s) is most suitable for compression, using measured or obtained metrics. The file compression/decompression system can compare, rank, or otherwise utilize the metrics corresponding to each individual compressor and/or compression configuration and selects a preferred compressor and/or compression configuration. For example, a compressor and associated configurations may be most suitable or preferred for compression when the compression comprises a higher or best compression ratio and/or a faster processing time relative to the other of the plurality of selected compression types. According to an embodiment, the different compressor configurations and the corresponding metrics can be presented to a user through a user interface in order to facilitate the manual selection of the compressor to be applied on an attribute.

According to an embodiment, storage instructions 265 direct the system to generate a compression parameter data structure, such as a compression parameter data file. According to an embodiment, the generated compression parameter data structure comprises an identification of and/or specifications for the selected compressor and/or compression configuration(s) for at least the first identified attribute. The compression parameter data file can comprise any information necessary to utilize a compressor, including compressor settings and other information. The storage instructions 265 can also direct the system to store the generated compression parameter data structure such that the stored file can be retrieved and used for decompression of the compressed data file. The compression parameter data structure can be stored in a remote or local database which can be a component of or otherwise in communication with file compression/decompression system 200. For example, the compression parameter data structure can be stored together with the compressed data file, or stored with a reference to or from the compressed data file.

According to an embodiment, reporting instructions 266 direct the system to provide information about the compression, the data file, and/or the compressors via a user interface 240 of the system. The provided information can be any information described or otherwise envisioned herein. The system may provide the information to a user via any mechanism, including but not limited to a visual display, an audible notification, a text message, an email, a page, or any other method of notification.

Uniform Interface for Specifying a Compressor

According to an embodiment, the file compression/decompression system comprises a Compressor Parameter Set. A Compressor Parameter Set is a data structure that contains the compressor configuration, including all the instructions and default parameters, required for the encoding and decoding of attribute data, and should be stored along with the compressed data. Each compressor configuration carries a unique ID to be used for specifying its association with an attribute, and a sequence of compressor steps, each consisting of one or more of the following elements:

(i) a unique ID of the compressor step.
(ii) the type and ID of the algorithm to be applied in the step. According to an embodiment, there are two broad types of algorithms: transform and compression, which involve changing the format of data representation and converting fixed-length symbols into compressed bit streams by means of probabilistic modeling. The algorithm ID is a predefined code that references a known algorithm of the specified type. In order to process the data, all algorithms being referenced must be installed and made accessible to the encoder or decoder.
(iii) a list of default parameters to the algorithm. Each parameter is composed of a parameter name, a data type, the number of values in the parameter and the parameter value(s).
(iv) the number of input variables to the algorithm and the input variable names. Note that variable names are only used for referencing data objects to be passed from one compressor step to another. To the algorithm, it is the order of the input data objects, as specified by the order of the input variable names, that is recognized. For the first step, since the input data must be the raw attribute values, there is no need to specify an input variable name and the number of input variables can be set to 0. From the second step onwards, each input variable name must match with an output variable name in the previous steps.
(v) the number of output variables for holding the ordered list of data objects generated by the algorithm, and the state and name of each output variable. If an output variable requires no further processing, its state is complete, and its variable name can be omitted, since the data object should go directly to the output buffer of the compressor. If an output variable needs to be processed by a subsequent step, the variable state is incomplete and a variable name must be specified.
(vi) the number of dependency attributes whose values are needed for executing the algorithm. The IDs of the dependency attributes should be provided in the configuration of the associated attribute.

Referring to Table 1 is example syntax of Compressor Parameter Set, which captures the key elements of a compressor configuration as described above, and explanations on the semantics are provided following the table. Note that the name, ordering and data type of individual fields can be changed without any impact on the functionality. Regarding the notation of data type, u(n) denotes unsigned integer using n bits; u(v) denotes unsigned integer with the number of bits dependent on the value of other syntax elements; f(n) denotes fixed-pattern bit string using n bits; and st(v) denotes null-terminated string with a variable length.

TABLE 1

Compressor Parameter Set Syntax.

| Syntax | Type |
| --- | --- |
| compressor_parameter_set { | |
|   compressor_ID | u(8) |
|   n_compressor_steps | u(4) |
|   for (i=0; i<n_compressor_steps; i++) { | |
|     compressor_step_ID[i] | u(4) |
|     algorithm_ID[i] | u(5) |
|     use_default_pars[i] | u(1) |
|     if (!use_default_pars[i]){ | |
|       algorithm parameters(algorithm_ID) | |
|     } | |
|     n_in_vars[i] | u(4) |
|     for (j=0; j<n_in_vars[i]; j++){ | |
|       in_var_ID[i][j] | u(4) |
|       prev_step_ID[i][j] | u(4) |
|       prev_out_var_ID[i][j] | u(4) |
|     } | |
|     n_completed_out_vars[i] | u(4) |
|     for (j=0; j<n_completed_out_vars[i]; j++) { | |
|       completed_out_var_ID[i][j] | u(4) |
|     } | u(4) |
|   } | |
|   while(!byte_aligned( )) { | |

TABLE 1-continued

Compressor Parameter Set Syntax.

| Syntax | Type |
|---|---|
| nesting_zero_bit<br>}<br>} | f(1) |

According to an embodiment are the following Compressor Parameter Set semantics:
  compressor_ID is the unique identifier of the compressor within the annotation table. Note that the value 0 is reserved for no compression.
  n_compressor_steps is the total number of processing steps in this compressor configuration. For each compressor step i, the following fields are specified: (i) compressor_step_ID[i] is the identifier of the compressor step; (ii) algorithm_ID[i] is the identifier of the algorithm to be applied in this step. Each algorithm type should have its own ID map; (iii) use_default_pars[i] is a flag, if set to one, indicates default parameters of the algorithm are used and therefore no changes to the parameters are needed.
  n_in_vars[i] is the number of input variables for the algorithm. For the first step (i==0), its value should be set to 0, since the input must be the raw attribute values.
  For each input variable j for the algorithm, the following fields are specified: (i) in_var_ID[i][j] is the predefined ID of an input variable known to the algorithm; and (ii) prev_step_p_ID[i][j], prev_out_var_ID[i][j] are respectively the ID of the previous compressor step and the ID of the corresponding output variable that contains the data to be passed to the current algorithm through the input variable specified by in_var_ID [i]
  n_completed_out_vars[i] is the number of completed output variables of the algorithm that require no further processing and can go directly to the output buffer of the compressor.
  completed_out_var_ID[i][j] specifies the predefined ID of an output variable known to the algorithm that is completed and requires no further processing.
  nesting_zero_bit is one bit set to 0 inserted as necessary to ensure byte alignment of the data structure.

According to an embodiment, Algorithm Parameters is a data structure for specifying the parameter settings of the algorithm referenced by algorithm_ID. Referring to Table 2 is a table of example syntax for the Algorithm Parameters.

TABLE 2

Algorithm Parameters Syntax.

| Syntax | Type | Remarks |
|---|---|---|
| algorithm parameters(algorithm_ID) {<br>  n_pars<br>  for (i = 0; i < n_pars; i++) {<br>    par_ID[i]<br>    par_type[i]<br>    par_num_array_dims[i]<br>    for (j = 0; j < par_num_array_dims; j++) {<br>      par_array_dims[i][j]<br>    }<br>    if (par_num_array_dims[i] == 0) {<br>      par_val[i] | u(4)<br><br><br>u(4)<br>u(8)<br>u(2)<br><br>u(8)<br><br><br>u(v) | <br><br><br><br><br><br><br><br><br>v dependent on the parameter data type |
|     } else if (par_num_array_dims[i] == 1) {<br>      for (j = 0; j < par_array_dims[i][0]; j++) {<br>        par_val[i][j] | <br><br>u(v) | <br><br>v dependent on the parameter data type |
|       }<br>    } else if (par_num_array_dims[i] == 2) {<br>      for (j = 0; j < par_array_dims[i][0]; j++) {<br>        for (k = 0; k < par_array_dims[i][1]; k++) {<br>          par_val[i][j][k] | <br><br><br><br>u(v) | <br><br><br><br>v dependent on the parameter data type |
|         }<br>      }<br>    } else if (par_num_array_dims[i] == 3) {<br>      for (j = 0; j < par_array_dims[i][0]; j++) {<br>        for (k = 0; k < par_array_dims[i][1]; k++) {<br>          for (k = 0; k < par_array_dims[i][2]; k++) {<br>            par_val[i][j][k][1] | <br><br><br><br><br><br>u(v) | <br><br><br><br><br><br>v dependent on the parameter data type |
|           }<br>        }<br>      }<br>    }<br>  }<br>} | | |

According to an embodiment are the following Algorithm Parameters semantics:
  n_pars is the number of parameters that need to be modified for executing the algorithm referenced by algorithm_ID. Its value must not be greater than the number of parameters defined in the algorithm.
  For each parameter i being modified, the following fields are required: (i) par_ID[i] is the ID of one of the parameters defined in the algorithm; (ii) par_type[i] is the data type ID of the parameter; (iii) par_num_array_dims[i] is the number of dimensions of the parameter, 0 if it is a scalar value; (iv)

par_array_dims[i][ ] contains elements each specifying the size of an array dimension. It is omitted if attribute_num_array_dims=0; (v) par_val[i][ ][ ][ ] contains the parameter value(s). Its number of dimensions is equal to (par_array_dims+1) and any extra dimensions can be omitted.

Uniform Interface for Specifying a Data Attribute and Associated Compressor Configuration According to an embodiment, the file compression/decompression system comprises an Attribute Parameter Set. An Attribute Parameter Set is a data structure that contains the configuration of an attribute, including some basic information and the compressor settings for its processing. The following are the key elements; (i) a unique ID and name of the attribute; (ii) data type information, and default and missing values of the attribute; (iii) the ID of the compressor for the processing of the attribute, it must be one of the compressor IDs defined in compressor parameter sets; (iv) modifications to selected parameters of the compressor steps; and (v) the IDs of the dependency variables (attributes or descriptors), whose data are needed for processing by some compressor steps.

Referring to Table 3 is an example syntax of Attribute Parameter Set, which captures the key elements of an attribute configuration as described above, and explanations on the semantics are provided following the table. Note that the name, ordering and data type of individual fields can be changed without any impact on the functionality. The data type notation is the same as Table 1. The Attribute Parameter Set contains the definitions of additional attributes, including their parameters, grouping, ordering and associated compressors.

TABLE 3

Attribute Parameter Set Syntax.

| Syntax | Type |
| --- | --- |
| attribute_parameter_set { | |
|   attribute_ID | u(16) |
|   attribute_name_len | u(8) |
|   attribute_name | c(attribute_name_len) |
|   attribute_type | u(8) |
|   attribute_num_array_dims | u(2) |
|   for (i = 0; i < attribute_num_array_dims; i++) { | |
|     attribute_array_dims[i] | u(8) |
|   } | |
|   attribute_default_value | st(v) |
|   attribute_missing_value | st(v) |
|   compressor_ID | u(8) |
|   n_steps_with_dependencies | u(4) |
|   for (i = 0; i < n_steps_with_dependencies; i++) { | |
|     compressor_step_ID[i] | u(4) |
|     n_dependencies[i] | u(4) |
|     for (j = 0; j < n_dependencies[i]; j++) { | |
|       dependency_var_ID[i][j] | u(4) |
|       dependency_is_attribute[i][j] | u(1) |
|       if (dependency_is_attribute[i][j]) { | |
|         dependency_ID[i][j] | u(16) |
|       } else { | |
|         dependency_ID[i][j] | u(7) |
|       } | |
|     } | |
|   } | |
|   while(!byte_aligned( )) { | |
|     nesting_zero_bit | f(1) |
|   } | |
| } | |

According to an embodiment are the following Attribute Parameter Set semantics:

attribute_ID is the identifier of the attribute, unique within an annotation parameter set.

attribute_name_len is the length of the attribute name.

attribute_name is the name of the attribute with length attribute_name_len.

attribute_type specifies the data type of the attribute.

attribute_num_array_dims specifies the number of array dimensions of an attribute entry, 0 if it is a scalar value.

attribute_array_dims[ ] contains elements each specifying the size of an array dimension. It is omitted if attribute_num_array_dims=0.

attribute default value is the default value of the attribute (i.e., it can be used for sparse encoding when most values equal to the default are excluded).

attribute missing value is the missing value of the attribute to be used in place of a null value in the output after the decoding process.

compressor_ID is the a compressor_ID as defined in the compressor_parameter_set used for the processing of the current attribute.

n_steps_with_dependencies is the number of steps in the compressor referenced by compressor_ID that involve dependency variables.

For each compressor step i with dependency variable(s) that need to be specified; (i) compressor_step_ID[i] is the ID of the compressor step; and (ii) n_dependencies[i] is the number of dependency variables required by the algorithm of the compressor step.

For each dependency variable j of the algorithm; (i) dependency_var_ID[i][j] is the predefined ID of the dependency variable known to the algorithm; (ii) dependency_is_attribute[i] [j] is a flag, if set to one, indicates the dependency data is stored in an attribute; otherwise, the dependency data is stored as a descriptor; and (iii) dependency_ID[i][j] specifies the ID of the attribute or descriptor containing the dependency data. Note that the length of the ID is 16 bits for attribute and 8 bits for descriptors.

nesting_zero_bit is one bit set to 0 inserted as necessary to ensure byte alignment of the data structure.

Encoding Algorithm Based on Compressor Configuration

According to an embodiment, the encoding of the raw attribute data is done by the sequential execution of the compressor steps defined in the associated compressor configuration. The encoding algorithm is outlined as follows:

1. Retrieve the configurations (parameter sets) of the attribute being processed and its associated compressor.
2. Obtain the compressor settings customized for the attribute by overriding the default parameter values from the compressor configuration with the attribute-specific parameter values in the attribute configuration.
3. Sequentially execute each compressor step from the first to the last. For each compressor step i:
   a. Look up the transform/compression algorithm using the algorithm_ID.
   b. If the algorithm_ID cannot be found, prompt the user for permission to download and install the corresponding algorithm from an authenticated software repository through a secure transmission channel.
   c. If there are any dependency variables defined for the step, obtain the decoded data of the dependency variables from the corresponding attributes or descriptors specified by dependency_is_attribute[i] [ ] and dependency_ID[i][ ].
   d. Apply the transform/compression algorithm on the data objects of the input variables using the parameter values and the data objects of the dependency variables associated with the step. If it is the first step, the raw attribute data is the only input data object being processed. The generated outputs consist of a list of data objects and their corresponding variable IDs.

e. If an output variable is specified as completed, then its data object should be placed in the output buffer of the compressor. Otherwise, it should be stored in a data map to be looked up through its step and variable IDs by a subsequent step for further processing. Note that each encoded data block/object is stored using the typed_data structure, as specified herein, to preserve its data type and array form.

TABLE 4

Typed Data Syntax.

| Syntax | Type | Remarks |
|---|---|---|
| typed_array_data { | | |
|   data_type_ID | u(8) | ID of the data type |
|   num_array_dims | u(2) | Number of array dimensions, 0 for scalar value |

TABLE 4-continued

Typed Data Syntax.

| Syntax | Type | Remarks |
|---|---|---|
|   n_elements = 1 | | |
|   for (i = 0; i < num_array_dims; i++) { | | |
|     array_dims[i] | u(32) | Size of the $i^{th}$ array dimension |
|     n elements = n_elements * array_dims[i] | | Number of elements in the array |
|   } | | |
|   for (i = 0; i < n_elements; i++) { | | |
|     data_block[i] | u(v) | v depends on the number of bits of the data type ID |
|   } | | |
| } | | | f. For the last step, return the content of the output buffer, which is a concatenation of the encoded blocks.

Pseudo-codes of the above attribute data encoding algorithm based on the associated compressor configuration are provided in Table 5, in accordance with an embodiment.

TABLE 5

Pseudo-codes of the Attribute Data Encoding Algorithm.

```
encode attribute(attribute_ID) {
  data_map = new Map( )      // Repository of intermediate data objects
  out_buffer = new List( )    // Output data buffer
  // Execute the compressor steps from the first to the last.
  for (i=0; i<n_compressor_steps; i++) {
    if (i == 0) {
      // If it is the first step, the raw attribute data is the only
      // input data object to be processed.
      in_data[0] = attribute_stream
    } else {
      // For the second step onwards, the input data objects to be processed
      // come from data objects generated by previous steps. The objects are
      // stored in a data map and can be looked up through their variable names.
      in data = NULL
      for (j=0; j<n_in_vars[i]; j++) {
        key = {prev_step_ID[i][j], prev_out_var_ID[i][j]}
        in_data[j] = data_map.get(key)
        data_map.remove(key)
      }
    }
    // Retrieve data objects of the dependency variables if there are any.
    dependency_data[ ] = NULL
    for (j=0; j<n_dependencies[i]; j++) {
      dependency_data[j] = get_decoded_data(
          dependency_is_attribute[i][j], dependency_ID[i][j])
    }
    // Apply the algorithm specified by algorithm_ID[i] on the input data objects specified by
    // in_var_ID[i][ ] and in_data[ ], using the parameter values specified by par_ID[i][ ] and
    // par_val[i][ ][ ][ ][ ], and any required dependency data objects specified by
    // dependency_var_ID[i][ ] and dependency_data[ ].
    {out_var_ID[ ], out_data[ ]} = apply(algorithm_ID[i], in_var_ID[i][ ], in_data[ ],
        par_ID[i][ ], par_val[i][ ][ ][ ][ ], dependency_var_ID[i][ ], dependency_data[ ])
    // Write any completed output data objects that require no further processing to the
    // output buffer.
    for (j=0; j<n_completed_out_vars[i]; j++) {
      for (k=0; k < size(out_var_ID); k++) {
        if (out_var_ID[k] == completed_out_var_ID[i][j]) {
          out_buffer.add(out_data[k])
        }
      }
    }
    // Store any incomplete output data objects that require further processing in data_map
    // with {compressor_step_ID[i], out_var_ID[j]} as its key.
    for (j=0; j<size(out_var_ID); j++) {
      out_var_complete = 0
      for (k = 0; k<n_completed_out_vars[i]; k++) {
        if (out_var_ID[j] == completed_out_var_ID[i][k]) {
          out_var_complete = 1
```

TABLE 5-continued

Pseudo-codes of the Attribute Data Encoding Algorithm.

```
            break
         }
      }
   }
   if (out_var_complete == 0) {
      key = {compressor_step_ID[i], out_var_ID [j]}
      data_map.add(key, out_data[j])
      }
   }
}
// The encoded data is given by the serialized byte stream of the output buffer.
encoded_data = out_buffer.stream( )
return encoded_data
}
```

Decoding Algorithm Based on Compressor Configuration

According to an embodiment, the file compression/decompression system comprises an attribute decoding process. The decoding of the compressed attribute data involves the reversal of the compressor steps defined in the associated compressor configuration by performing step-by-step inverse operations of the algorithms starting from the last step to the first step. The decoding algorithm is outlined as follows:

1. Retrieve the configurations (parameter sets) of the attribute being processed and its associated compressor.
2. Extract from the compressed attribute stream one or multiple encoded blocks, each corresponding to a completed output variable defined in a compressor step. Each encoded block is stored using the typed_data structure, as specified in Table 4, to preserve its data type and array form.
3. Perform the inverse operation of each compressor step in reverse order, starting from the last step until reaching the first step. For each compressor step i:
   a. Collect all input variable data of the current step either from the encoded blocks in step 2 above or from the output variable(s) of its upstream decoding step.
   b. If there are any dependency variables defined for the current step, obtain the decoded data of the dependency variables from the corresponding attributes or descriptors specified by dependency_is_attribute[i] [ ] and dependency_ID[i][ ].
   c. Retrieve from the compressor parameter set any changes to the default parameter settings for the current step.
   d. Apply an inverse operation of the algorithm specified for the current step on the input variable data using the associated parameter settings and any dependency variable data.
   e. If it has not reached the first step, store the output variable data to be further processed by subsequent decoding steps using the pair of step ID and variable ID as key for lookup.
   f. If it has reached the first step, fill in any missing values and return the output variable data of the inverse operation as the attribute data decoded by the compressor.

The steps of the attribute decoding process based on the associated compressor configuration are provided in the table below. Note that the initial value of attribute_stream is the encoded attribute data in a tile referenced by its indices. Other variables not declared or initialized within the codes are defined in the Compressor Parameter Set referenced by the compressor ID associated with the attribute.

TABLE 6

Attribute Decoding Process.

```
decode_attribute_payload(attribute_ID) {
      encoded_block[ ] = extract_encoded_blocks(attribute_stream)
      ptr = size(encoded_block)        // Pointer to encoded_block[ ]
      data_map = new Map( )             // Repository of intermediate data objects
      // Perform inverse operations of the algorithms defined the compressor steps
      // in reverse order, from last to first.
      for (i=(n_compressor_steps - 1); i>=0; i -- ) {
         // Collect the input data for the current step.
         idx = 0
         for (j = i + 1; j <n_compressor_steps; j++) {
            for (k = 0; k < n_in_vars[j]; k++) {
               if (prev_step_ID[j][k] == i) {
                  curr_in_var_ID[idx] = prev_out_var_ID[j][k]
                  key = {j, in_var_ID[j][k]}
                  curr_in_var_data[idx] = data_map.get(key)
                  idx++
               }
            }
         }
         ptr -= n_complete_out_vars[i]
         for (j = 0; j <n_complete_out_vars[i]; j++) {
            curr_in_var_ID[idx] = complete_out_var_ID[i][j]
            curr_in_var_data[idx] = encoded_block[ptr + j]
            idx++
         }
```

TABLE 6-continued

Attribute Decoding Process.

```
   // Retrieve dependency data from the Attribute Parameter Set referenced by
   // attribute ID.
   idx = 0
   n_steps_with_dependencies
   for (j = 0; j < n_steps_with_dependencies; j++) {
      if (compressor_step_ID[j] == i) {
         for (k = 0; k < n_dependencies[j]; j++) {
            curr_depend_var_ID[idx] = dependency_var_ID[j][k]
            curr_depend_var_data[idx] = get_decoded_data(
                dependency_is_attribute[j][k], dependency_ID[j][k])
         }
      }
   }
   // Retreive parameter data for the current step from the Compressor Parameter
   // Set referenced by the compressor ID associated with the attribute.
   [curr_par_ID[ ], curr_par_data[ ]] = get_parameters(compressor_ID, i)
   // Apply inverse operation of the algorithm referenced by algorithm_ID[i]
   // using the retrieved input, dependency and parameter data.
   [curr_out_var_ID[ ], curr_out_var_data[ ]] = apply_inverse(algorithm_ID[i],
         curr_in_var_ID, curr_in_var_data, curr_depend_var_ID,
         curr_depend_var_data, curr_par_ID, curr_par_data)
   if (i == 0) {
      // If it has reached the first compressor step, the data object generated
      // by the inverse operation is the decoded attribute.
      attribute_stream = curr_out_var_data[0]
   } else {
      // If it has not reached the first compressor step, each data object
      // curr_out_var_data[j] generated by the inverse operation is placed in
      // data_map with the pair of current step ID and curr_out_var_ID[j] as
      // its key for lookup by a subsequent step.
      for (j = 0; j < size(curr_out_var_ID); j++) {
         key = {i, curr_out_var_ID[j]}
         data_map.add(key, curr_out_var_data[j])
      }
   }
}
// Fill in any missing values in the output symbols.
decoded_symbols[31][attribute_ID][tile_index_1][tile_index_2] =
      fill_missing_values(attribute_stream, attribute_missing_value)
}
```

Mechanism for Automatic Determination of Compressor Configurations

While for known and prevalent file types, compressor configurations can be pre-defined by a group of data compression experts and adopted for use by the community, there are times when compressor configurations need to be specified, for example, when handling new or exclusive file types, or when a file of known type allows the inclusion of unplanned attributes. One possible way is to let a user manually specify the compressor configurations, perhaps with the assistance of a graphical tool that offers different options and explanations. This approach, however, requires much user knowledge and experience on data compression, and often results in suboptimal configurations.

Accordingly, provided is a mechanism for the automatic determination of compressor configurations based on performance. The system can comprise a list of available transform and compression algorithms available for selection, and for each is known the types of data the algorithm can handle and the possible connections between the algorithms. The mechanism can work as follows. For each attribute in the file:

1. With the knowledge of the available algorithms and additional constraints such as the maximum allowed number of compressor steps and the prohibition of cycles in the sequence of steps, identify all possible compressor configurations for the attribute.
2. Evaluate the performance of each compressor configuration with metrics such as compression ratio and processing time. It can be done on a subset of data from the file being compressed, or on a training file to build a compressor configuration template for a specific file type. To speed up the process, the evaluations can be run in parallel.
3. Select the best compressor configuration for the attribute based on performance criteria such as one with the highest compression ratio and a processing time that falls in the first quartile among all configurations.

After selecting the best compressor configuration for each attribute:

4. Generate the attribute and compressor parameter set data structures that contain all instructions and parameters needed for the processing of the file.
5. If the generated attribute and compressor configurations are meant to be applied to other files of the same type, their data structures can be stored in a repository, and looked up for use in the future by file type or file extension.
6. To compress a file, an encoder can apply the aforementioned encoding algorithm on each attribute using the generated configurations, and store the configuration data structures along with the compressed attribute data.
7. To decode a compressed file, a decoder can apply the aforementioned decoding algorithm on each attribute using the configuration data that comes with the file.

Example 1—Compressor Configuration for Sparse Expression Data

The following is a non-limiting example applying attribute and compressor configurations for the compression of sparse single-cell RNA expression data. Two compressor configurations were evaluated.

TABLE 7

Compressor Configuration 1 for Compression of Single-Cell Expression Data

| Step | Algorithm | in_var_name | n_out_vars | out_var_name | out_var_complete |
|---|---|---|---|---|---|
| 1 | Sparse Transform | (Input: Matrix of Raw Attribute Values) | 3 | ["row_idx", "col_idx", "value"] | [0, 0, 0] |
| 2 | BSC Compression | ["row_idx"] | 1 | [""] | [1] |
| 3 | BSC Compression | ["col_idx"] | 1 | [""] | [1] |
| 4 | BSC Compression | ["value"] | 1 | [""] | [1] |

For Compressor Configuration 1 summarized in Table 7, the input matrix of expression values first undergoes Sparse Transform that generates three output variables: row_idx, col_idx and value, which only register cells with non-zero values. BSC compression is then applied independently on each of the output variables from step 1, resulting in an encoded data stream that consists of three data blocks concatenated in the order as they are defined in the compressor steps.

TABLE 8

Compressor Configuration 2 for Compression of Single-Cell Expression Data

| Step | Algorithm | in_var_name | n_out_vars | out_var_name | out_var_complete |
|---|---|---|---|---|---|
| 1 | Sparse Transform | (Input: Matrix of Raw Attribute Values) | 3 | ["row_idx", "col_idx", "value"] | [0, 0, 0] |
| 2 | Delta Transform | ["row_idx"] | 1 | ["row_idx_delta"] | [0] |
| 3 | BSC Compression | ["row_idx_delta"] | 1 | [""] | [1] |
| 4 | RLE Transform | ["col_idx"] | 2 | ["col_idx_value", "col_idx_count"] | [0, 0] |
| 5 | BSC Compression | ["col_idx_val"] | 1 | "" | [1] |
| 6 | BSC Compression | ["col_idx_count"] | 1 | "" | [1] |
| 7 | BSC Compression | ["value"] | 1 | "" | [1] |

For Compression Configuration 2 summarized in Table 8, like the first configuration, the input matrix of expression values first undergoes Sparse Transform that generates three output variables: row_idx, col_idx and value. Delta Transform is applied on row_idx to generate delta values stored in the variable row_idx_delta, which are then compressed by the BSC algorithm. Run Length Encoding (RLE) is applied on col_idx to generate two output variables: col_idx_val and col_idx_count, which are then independently compressed by BSC. Data in the value variable from step one is directly compressed by BSC. This results in an encoded data stream that consists of four data blocks concatenated as they are defined in the compressor steps.

To evaluate the performance, the two compressor configurations were applied to single-cell RNA expression data stored in a file of Market Matrix format, with a size of 152 MB before compression. After direct compression by Gzip and BSC, the file size became 47 MB and 42 MB respectively.

Table 9 summarizes the various data sizes after applying Compressor Configurations 1 and 2 using the encoding algorithm. With reference to the file size of 42 MB after direct compression by BSC, the compression ratios of Compressor Configurations 1 and 2 are respectively 5.19 and 3.68. Since Compressor Configuration 1 has a better performance in terms of compression ratio, it should be selected for use on the compression of sparse expression data in general.

TABLE 9

Compressed Data Size for Compressor Configurations 1 and 2

| Compressor Configuration | Step | Variable Name | Block Size After BSC Compression | Overall Data Size After BSC Compression |
|---|---|---|---|---|
| 1 | 2 | row_idx | 5.1 MB | 8.1 MB |
|   | 3 | col_idx | 27 KB |   |
|   | 4 | value | 3.1 MB |   |
| 2 | 3 | row_idx_delta | 8.3 MB | 11.4 MB |
|   | 5 | col_idx_val | <1 KB |   |
|   | 6 | col_idx_count | 12 KB |   |
|   | 7 | value | 3.1 MB |   |

The example demonstrates that the method significantly reduces the size of the compressed data file relative to prior art methods (such as direct compression by BSC). This improves the functionality and efficiency of the file compression/decompression system, and revolutionizes storage capabilities of a computer system or database. Further, when dealing with a file comprising millions or billions of data points for each of one or more attributes, compression comprises millions or billions of calculations, something the human mind is not equipped to perform, even with pen and pencil.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for compressing a data file using a file compression and decompression system, comprising:
  receiving a genomic data file for compression, the genomic data file comprising a plurality of different attributes;
  identifying a first attribute of the plurality of different attributes, and storing a specification of the identified first attribute in an attribute parameter data structure;
  selecting, based on the identified first attribute, a plurality of compression types and/or compression configurations from a predetermined plurality of compression types and compression configurations;
  compressing at least some of the data from the received data file for the identified first attribute using each of the selected plurality of compression types and/or compression configurations, individually, wherein one or more metrics are measured for each individual compression;
  determining, based on the one or more metrics of each of the individual compressions, which one of the selected plurality of compression types and/or compression configurations is most suitable for compression;
  generating a compression parameter data structure comprising an identification of the one of the selected plurality of compression types and/or compression configurations most suitable for compression of the identified first attribute;
  compressing, using the identified compression type, the data from the received genomic data file for the first attribute to generate a compressed genomic data file;
  storing the attribute parameter data structure, the compression parameter data structure, and the compressed data file, wherein the stored compression parameter data structure is configured to be retrieved and used for decompression of the compressed genomic data file and providing via a user interface, one or more of: (i) information about the generated compression parameter data structure and/or the compressed genomic data file, and (ii) information about one or more of the identified compression types and/or compression configurations such that the user can select a compressor type and/or configuration to be applied to compress an attribute.

2. The method of claim 1, further comprising:
repeating the identifying, selecting, compression, and determining steps for at least a second attribute of the plurality of different attributes, wherein the compression parameter data structure comprises a specification of a one of the selected plurality of compression types and/or compression configurations most suitable for compression of the identified second attribute.

3. The method of claim 1, further comprising the step of decompressing the stored compressed genomic data file, wherein decompression comprises consulting the compression parameter data structure to identify a decompression type for the first attribute.

4. The method of claim 1, wherein each of the selected plurality of compression types and/or compression configurations is selected because it is capable of compressing the data from the received genomic data file for the identified first attribute.

5. The method of claim 1, wherein the data file is a genomic data file.

6. The method of claim 1, wherein the one or more metrics comprises one or more of compression ratio and processing time for said compression.

7. The method of claim 1, wherein a compression type is most suitable when the corresponding compression comprises a higher compression ratio and/or a faster processing time relative to the other of the plurality of selected compression types and/or compression configurations.

8. The method of claim 1, further comprising the step of providing, via a user interface, information about the generated compression parameter data structure and/or the compressed data file.

9. The method of claim 1, further comprising the step of providing to a user, via a user interface, information about one or more of the identified compression types and/or compression configurations such that the user can select a compressor type and/or configuration to be applied to compress an attribute.

10. A system for compressing a data file, comprising:
a genomic data file for compression, the genomic data file comprising a plurality of different attributes;
a processor configured to: (i) identify a first attribute of the plurality of different attributes and store a specification of the identified first attribute in an attribute parameter data structure; (ii) select, based on the identified first attribute, a plurality of compression types and/or compression configurations from a predetermined plurality of compression types and/or compression configurations; (iii) compress at least some of the data from the received data file for the identified first attribute using each of the selected plurality of compression types and/or compression configurations, individually, wherein one or more metrics are measured for each individual compression; (iv) determine, based on the one or more metrics of each of the individual compressions, which one of the selected plurality of compression types and/or compression configurations is most suitable for compression; (v) generate a compression parameter data structure comprising an identification of the one of the selected plurality of compression types and/or compression configurations most suitable for compression of the identified first attribute; (vi) compress, using the identified compression type, the data from the received data file for the first attribute to generate a compressed data file; and (vii) store the attribute parameter data structure, the compression parameter data structure, and the compressed data file, wherein the stored compression parameter data structure is configured to be retrieved and used for decompression of the compressed genomic data file;
and a user interface configured to provide one or more of: (i) information about the generated compression parameter data structure and/or the compressed genomic data file, and (ii) information about one or more of the identified compression types and/or compression configurations such that the user can select a compressor type and/or configuration to be applied to compress an attribute.

11. The system of claim 10, wherein the processor is configured to repeat the identifying, selecting, compression, and determining steps for at least a second attribute of the plurality of different attributes, wherein the compression parameter data structure comprises an identification of a one of the selected plurality of compression types and/or compression configurations most suitable for compression of the identified second attribute.

12. The system of claim 10, wherein the processor is configured to decompress the stored compressed genomic data file, wherein decompressing comprises consulting the compression parameter data structure to identify a decompression type for the first attribute.

13. The system of claim 10, wherein each of the selected plurality of compression types and/or compression configurations is selected because it is capable of compressing the data from the received genomic data file for the identified first attribute.

14. The system of claim 10, wherein the one or more metrics comprises one or more of compression ratio and processing time for said compression.

* * * * *